(12) United States Patent
Padmanabhan et al.

(10) Patent No.: US 12,366,584 B2
(45) Date of Patent: Jul. 22, 2025

(54) IDENTIFICATION OF PLATELET ACTIVATING ANTIBODIES

(71) Applicant: RETHAM TECHNOLOGIES, INC., Wauwatosa, WI (US)

(72) Inventors: Anand Padmanabhan, Rochester, MN (US); Curtis G. Jones, Wauwatosa, WI (US)

(73) Assignee: RETHAM TECHNOLOGIES, INC., Wauwatosa, WI (US)

( * ) Notice: Subject to any disclaimer, the term of this patent is extended or adjusted under 35 U.S.C. 154(b) by 363 days.

(21) Appl. No.: 17/234,182

(22) Filed: Apr. 19, 2021

(65) Prior Publication Data
US 2021/0325405 A1 Oct. 21, 2021

Related U.S. Application Data

(60) Provisional application No. 63/013,056, filed on Apr. 21, 2020.

(51) Int. Cl.
| | |
|---|---|
| *G01N 33/86* | (2006.01) |
| *C12N 5/078* | (2010.01) |
| *G01N 1/28* | (2006.01) |
| *G01N 33/545* | (2006.01) |
| *G01N 33/564* | (2006.01) |
| *G01N 33/68* | (2006.01) |

(52) U.S. Cl.
CPC ........... *G01N 33/86* (2013.01); *C12N 5/0644* (2013.01); *G01N 1/28* (2013.01); *G01N 33/545* (2013.01); *G01N 33/564* (2013.01); *G01N 33/6857* (2013.01); *C12N 2500/42* (2013.01); *C12N 2501/30* (2013.01); *C12N 2501/998* (2013.01); *C12N 2523/00* (2013.01)

(58) Field of Classification Search
CPC .... G01N 33/545; G01N 33/6857; G01N 1/28; G01N 33/86; G01N 33/564; G01N 2333/70564; G01N 2800/222
See application file for complete search history.

(56) References Cited

U.S. PATENT DOCUMENTS

| | | | |
|---|---|---|---|
| 5,466,582 A | 11/1995 | Amiral | |
| 5,972,718 A | 10/1999 | Moghaddam | |
| 9,097,731 B2 | 8/2015 | Amiral et al. | |
| 9,851,367 B2* | 12/2017 | Aster | G01N 33/56966 |
| 10,215,767 B2* | 2/2019 | Aster | G01N 33/56966 |
| 2005/0032142 A1 | 2/2005 | Cohen et al. | |
| 2007/0190582 A1* | 8/2007 | Poncz | G01N 33/86 |
| | | | 435/7.21 |
| 2014/0038207 A1* | 2/2014 | Tomer | G01N 33/566 |
| | | | 435/7.21 |

OTHER PUBLICATIONS

Horne et al. Platelet binding of IgG from patients with heparin-induced thrombocytopenia. J Lab Clin Med 127: 435-442 (1996).*
Bakchul T. Expert Opin Drug Saf. 2016; 15:787-797.
Greinacher A. N Engl J Med. 2015; 373:1882-1884.
Arepally M G. Blood. 2017; 129:2864-2872.
Amiral J. Semin Hematol. Jan. 1999;36(1 Suppl 1):7-11.
Hogan M, Berger J S. Vasc Med. 2020; 25:160-173.
Warkentin T E. Int J Lab Hematol. 2019; 41:15-25.
Dhakal B, et al. Lancet Haematol. 2018; 5:220-231.
Amiral J, et al. Blood. 1996; 88:410-416.
Regnault V, et al. Blood. 2003; 101:1419-1421.
Padmanabhan A, et al. Blood. 2015; 125:155-151.
Paniccia et al., "Platelet function tests: a comparative review", Vascular Health and Risk Management, 2015, vol. 11, pp. 133-148.
Kamath et al., "Platelet activation: assessment and quantification", European Heart Journal, vol. 22, 2001, pp. 1561-1571.
Kunicki et al., "Human Platelet Fibrinogen: Purification and Hemostatic Properties", Blood, 1985, vol. 66, No. 4, pp. 808-815.
Whiteheart, "Platelet granules: surprise packages", Blood, 2011, vol. 118, No. 5, pp. 1190-1191.
O'Connor et al., "Proteomics Strategy for Identifying Candidate Bioactive Proteins in Complex Mixtures: Application to the Platelet Releasate", Journal of Biomedicine and Biotechnology, 2010, 13 pages.
International Search Report and Written Opinion for Application No. PCT/US2021/037699 dated Nov. 2, 2021 (15 pages).
Padmanabhan A, et al. Chest 2016; 150:506-515.
Padmanabhan A, et al. Thromb. Haemost. 2015; 114:1322-1323.
Samuelson Bannow BT, et al. Blood. 2021; 137:1082-1089.

* cited by examiner

*Primary Examiner* — Gailene Gabel
(74) *Attorney, Agent, or Firm* — Michael Best & Friedrich LLP (57) ABSTRACT

Described is a method for identifying pathogenic platelet-activating antibodies in a subject's blood and particularly antibodies implicated in heparin-induced thrombocytopenia (HIT) which comprises the preparation of a platelet releasate from a normal subject's platelets, the combination of the platelet release with a normal subject's platelets, a test subject's blood sample, and analyzing the sample for platelet activation.

26 Claims, 2 Drawing Sheets

IDENTIFICATION OF PLATELET ACTIVATING ANTIBODIES

FEDERALLY SPONSORED RESEARCH

This invention was made with United States government support under National Institutes of Health Small Business Innovation Research (SBIR) grant number HL147734. The United States government has certain rights in the invention.

TECHNICAL FIELD

Described herein is a method for identifying pathogenic platelet-activating antibodies in a subject's blood and particularly antibodies implicated in heparin-induced thrombocytopenia (HIT). The method comprises the preparation of a platelet releasate from a normal subject's platelets, the combination of the platelet release with a normal subject's platelets, a test subject's blood sample, and analyzing the sample for platelet activation. Also described herein is a method for preparing a platelet releasate.

BACKGROUND

Heparin-induced thrombocytopenia (HIT) is an adverse reaction to heparin, in which affected subjects produce platelet-activating antibodies and develop thrombocytopenia. A subset of these individuals experiences arterial or venous thrombosis, which in severe cases can be life-threatening. Experts believe that up to 20,000 people per year develop HIT in the U.S. and leads to more than 5 deaths every day. Because early diagnosis and treatment can reduce morbidity, it is important that a timely and accurate diagnosis of HIT be made. An accurate diagnosis of HIT requires attention to both clinical findings and laboratory test results.

Conventional treatment for patients suspected of having HIT includes the immediate cessation of all heparin followed by prompt administration of a non-heparin, alternative anticoagulant such as a direct thrombin inhibitor. Such treatments involve additional hospitalization, a considerable expense, and a risk of severe bleeding of 1% per treatment day. Thus, an accurate diagnosis of HIT and characterization of thrombosis risk is critical for effective patient management.

HIT is caused by antibodies that recognize platelet factor 4(PF4), Interleukin 8 (IL8), neutrophil-activating peptide-2 (NAP-2), or other platelet proteins in a complex with heparin or other components of the platelet surface. Among available tests for HIT antibody detection, the serotonin release assay (SRA) is considered by many to correlate best with a clinical picture typical of HIT and is often used as a surrogate for HIT diagnosis. However, the SRA is performed routinely only in a few specialized laboratories because of the use of radioactivity, labor intensiveness, reliance on fresh platelets, and technical demands of the assay. An alternative, widely used diagnostic test, the PF4-based ELISA, is technically simple and highly sensitive for antibody detection but this assay lacks the necessary specificity to clinically diagnose HIT. Other recently developed HIT assays include tests such as the PEA that use PF4-treated platelets for HIT diagnosis. It remains unclear why some heparin-PF4 directed antibodies cause HIT, but many others do not. It is generally agreed, however, that antibodies testing positive in the SRA are most likely to be pathogenic and to cause thrombocytopenia as well as thrombosis, the most serious complication of HIT.

Accordingly, there is a need for an assay that identifies antibodies that activate platelets and can be efficiently performed in a clinical laboratory.

SUMMARY

One embodiment described herein is a method for identifying platelet-activating antibodies in a subject's blood sample, the method comprising: obtaining a blood sample from a subject suspected of having platelet-activating antibodies; combining a platelet releasate from one or more normal subjects with platelets from one or more normal subjects, and with the blood sample from the subject suspected of having platelet-activating antibodies and incubating the combination for a period of time; and measuring platelet activation; wherein platelet activation is indicative of the presence of platelet-activating antibodies in the blood sample from the subject suspected of having platelet-activating antibodies. In one aspect, the platelet-activating antibodies comprise platelet-activating heparin-induced thrombocytopenia antibodies. In another aspect, the blood sample from the subject suspected of having platelet-activating antibodies comprises one or more of whole blood, plasma, serum, or fractionated blood. In another aspect, the platelets have been stabilized for storage by one or more of cooling, freezing, chemical storage, or lyophilization. In another aspect, the period of time is about 15 min. to about 5 hours. In another aspect, the platelet releasate is prepared by: activating platelets from one or more normal subjects by the addition of an effective amount of a platelet activator and incubating for a period of time; collecting material released from the platelets upon activation to obtain a platelet releasate; optionally, incubating the platelet releasate at about 40° C. to about 75° C. for about 5 min. to about 10 hours; optionally, removing negatively charged ions from the platelet releasate with an anion-exchanger to obtain an anion-exchanger adsorbed platelet releasate. In another aspect, the period of time is about 5 min. to about 4 hours. In another aspect, the platelet releasate is incubated with the anion-exchanger for about 5 min. to about 4 hours. In another aspect, measuring platelet activation comprises one or more of: analyzing the release of platelet granule components; detecting the expression of cell surface markers that are expressed upon platelet activation; detecting increase in expression of p-selectin on the platelet; detecting an increase in binding of annexin V to the platelet, detecting an increased proteolytic cleavage of the platelet membrane protein Fc gamma RIIa (CD32); detecting a change in platelet shape; detecting an increased level of ionized calcium in the platelet cytoplasm; detecting changes in expression levels of one or more CD markers found on activated platelets; detecting a change in platelet integrin conformation; detecting a change in platelet membrane potential; detecting a change in platelet impedance; detecting platelet agglutination; detecting platelet aggregation; detecting activated-platelet metabolic state; or detecting activated-platelet metabolites or byproducts. In another aspect, measuring platelet activation comprises analyzing the expression of cell surface markers that are expressed upon platelet activation using fluorescence-based flow cytometry, radioimmunoassays (RIA), or enzyme-linked immunosorbent assays (ELISAs). In another aspect, the cell surface markers comprise one or more of selectins, integrins, or immunoglobulins. In another aspect, the cell surface markers comprise p-selectin. In another aspect, measuring platelet activation comprises analyzing the release of platelet granule components. In another aspect, the released platelet granule components comprise labeled serotonin. In another aspect, the method further comprises combining heparin or a heparin-like compound with the platelet releasate from one or more normal subjects, platelets from one or more normal subjects, the blood sample from the subject suspected of having platelet-activating antibodies. In another aspect, the heparin or heparin-like compound has a final concentration of about 0.05 U/mL to about 200 U/mL. In another aspect, the platelets from one or more normal subjects comprises one or more of isolated platelets, platelet-rich plasma, or washed platelets. In another aspect, the platelet releasate is incubated with the anion-exchanger for about 5 min. to about 4 hours. In another aspect, the platelet activation is compared to one or more controls comprising blood from a normal subject, historical data, or blood from a subject diagnosed as having platelet-activating antibodies. A normal subject is an individual who does not have Heparin-induced thrombocytopenia.

Another embodiment described herein is a method for identifying platelet-activating antibodies in a subject's blood sample, the method comprising: obtaining a blood sample from a subject suspected of having platelet-activating antibodies; combining a platelet releasate from one or more normal subjects with platelets from one or more normal subjects and incubating the combination for a first period of time; combining the blood sample from a subject suspected of having platelet-activating antibodies with the combination of platelet releasate and platelets from one or more normal subjects and incubating the second combination for a second period of time; measuring platelet activation; wherein platelet activation is indicative of the presence of platelet-activating antibodies in the blood sample from the subject suspected of having platelet-activating antibodies. In one aspect, the platelet-activating antibodies comprise platelet-activating heparin-induced thrombocytopenia antibodies. In another aspect, the blood sample from the subject suspected of having platelet-activating antibodies comprises one or more of whole blood, plasma, serum, or fractionated blood. In another aspect, the platelets have been stabilized for storage by one or more of cooling, freezing, chemical storage, or lyophilization. In another aspect, the first period of time is about 5 min. to about 1 hour. In another aspect, the second period of time is about 15 min. to about 5 hours. In another aspect, the platelet releasate is prepared by: activating platelets from one or more normal subjects by the addition of an effective amount of a platelet activator and incubating for a period of time; collecting material released from the platelets upon activation to obtain a platelet releasate; optionally, incubating the platelet releasate at about 40° C. to about 75° C. for about 5 min. to about 10 hours; optionally, removing negatively charged ions from the platelet releasate with an anion-exchanger to obtain an anion-exchanger adsorbed platelet releasate. In another aspect, the period of time is about 15 min. to about 4 hours. In another aspect, the platelet releasate is incubated with the anion-exchanger for about 5 min. to about 4 hours. In another aspect, measuring platelet activation comprises one or more of: analyzing the release of platelet granule components; detecting the expression of cell surface markers that are expressed upon platelet activation; detecting increase in expression of p-selectin on the platelet; detecting an increase in binding of annexin V to the platelet, detecting an increased proteolytic cleavage of the platelet membrane protein Fc gamma RII (CD32); detecting a change in platelet shape; detecting an increased level of ionized calcium in the platelet cytoplasm; detecting changes in expression levels of one or more CD markers found on activated platelets; detecting a change in platelet integrin conformation; detecting a change in platelet membrane potential; detecting a change in platelet impedance; detecting platelet agglutination; detecting platelet aggregation; detecting activated-platelet metabolic state; or detecting activated-platelet metabolites or byproducts. In another aspect, measuring platelet activation comprises analyzing the expression of cell surface markers that are expressed upon platelet activation using fluorescence-based flow cytometry, radioimmunoassays (RIA), or enzyme-linked immunosorbent assays (ELISAs). In another aspect, the cell surface markers comprise one or more of selectins, integrins, or immunoglobulins. In another aspect, the cell surface markers comprise p-selectin. In another aspect, measuring platelet activation comprises analyzing the release of platelet granule components. In another aspect, the released platelet granule components comprise labeled serotonin. In another aspect, the method further comprises combining heparin or a heparin-like compound with the platelet releasate from one or more normal subjects, platelets from one or more normal subjects, the blood sample from the subject suspected of having platelet-activating antibodies. In another aspect, the heparin or heparin-like compound has a final concentration of about 0.05 U/mL to about 200 U/mL. In another aspect, the platelets from one or more normal subjects comprises one or more of isolated platelets, platelet-rich plasma, or washed platelets. In another aspect, the platelet activation is compared to one or more controls comprising blood from a normal subject, historical data, or blood from a subject diagnosed as having platelet-activating antibodies.

Another embodiment described herein is a method of preparing a platelet releasate, the method comprising: obtaining platelets form one or more normal subjects; activating platelets from one or more normal subjects by the addition of an effective amount of a platelet activator and incubating for a period of time; collecting material released from the platelets upon activation to obtain a platelet releasate. In one aspect, the period of time is from about 15 min. to about 4 hours. In another aspect, the method further comprises incubating the platelet releasate at about 40° C. to about 75° C. for about 5 min. to about 10 hours. In another aspect, the method further comprises removing negatively charged ions from the platelet releasate with an anion-exchanger to obtain an anion-exchanger adsorbed platelet releasate. In another aspect, the platelet releasate is incubated with the anion-exchanger for about 5 min. to about 4 hours. In another aspect, the platelet activator is one or more of Thrombin Receptor Activating Peptide (TRAP), adenosine diphosphate (ADP), arachidonic acid, epinephrine, collagen, thrombin, thromboxane A2 (TxA2), thromboxane A2 (TXA2) mimetic U46619, calcium ionophore A23187, ristocetin, or rhodocytin.

Another embodiment described herein is a platelet releasate produced from the method described herein.

Another embodiment described herein is the use of the platelet releasate described herein for identifying platelet-activating antibodies in a blood sample from a subject suspected of having platelet-activating antibodies.

Another embodiment described herein is a means for identifying platelet-activating heparin-induced thrombocytopenia antibodies in a subject's blood, the means comprising: obtaining a blood sample from a subject suspected of having platelet-activating heparin-induced thrombocytopenia antibodies; obtaining platelets from one or more normal subjects; preparing a platelet releasate from platelets from one or more normal subjects, the method comprising: activating platelets from one or more normal subjects by the addition of an effective amount of a platelet activator and incubating for about 15 min. to about 4 hours; collecting material released from the platelets upon activation to obtain a platelet releasate; optionally, incubating the platelet releasate at about 40° C. to about 75° C. for about 5 min. to about 10 hours; and optionally, removing negatively charged ions from the platelet releasate with an anion-exchanger to obtain an anion-exchanger adsorbed platelet releasate; combining the platelet releasate with the platelets from one or more normal subjects and incubating the combination for about 5 min. to about 60 min; combining the blood sample from a subject suspected of having platelet-activating heparin-induced thrombocytopenia antibodies with the combination of the platelet releasate and the platelets from one or more normal subjects and incubating the second combination for about 15 min. to about 5 hours; measuring platelet activation; wherein platelet activation is indicative of the presence of platelet-activating antibodies in the blood sample from the subject suspected of having platelet-activating heparin-induced thrombocytopenia antibodies.

Another embodiment is a lateral flow immunochromatographic assay for detecting heparin-induced thrombocytopenia antibodies using the methods described herein.

Another embodiment described herein is a kit for identifying platelet-activating antibodies in a subject's blood sample, the kit comprising one or more of: (a) a container and means for collecting blood from a subject suspected of having platelet-activating antibodies; (b) a container comprising a platelet releasate from one or more normal subjects; (c) a container comprising platelets from one or more normal subjects; (d) a container for combing (a)-(c); (e) reagents for analyzing the presence of platelet-activating antibodies in the blood from a subject suspected of having platelet-activating antibodies; (f) one or more control samples comprising blood from a normal subject or blood from a subject diagnosed as having platelet-activating antibodies; or (g) instructions or directions for use.

Another embodiment described herein is a kit for preparing a platelet releasate, the kit comprising one or more of: (a) a container and means for obtaining blood from one or more normal subjects; (b) a means for isolating platelets from the one or more normal subject's blood; (c) a container for activating platelets; (d) a platelet activator; (e) an anion-exchange resin or cartridge; (f) a means for collecting the platelet releasate; or (f) instructions or directions for use.

DETAILED DESCRIPTION

"Identifying" or "diagnosing" as used herein refers to classifying a subject as having a pathology or a symptom, determining a severity of the pathology (grade or stage), monitoring pathology progression, or forecasting an outcome of a pathology or prospects of recovery. In one embodiment, a subject is identified or diagnosed as having platelet-activating antibodies in its blood. In one aspect, the platelet-activating antibodies comprise platelet-activating heparin-induced thrombocytopenia antibodies. The identification or detection of platelet-activating heparin-induced thrombocytopenia antibodies is indicative or diagnostic of the subject having heparin-induced thrombocytopenia (HIT).

"Heparin-induced thrombocytopenia" or "HIT" as used herein refers to an adverse reaction to heparin or thrombotic thrombocytopenic reactions occurring in the absence of heparin exposure such as Spontaneous HIT and VITT (Vaccine-induced immune thrombocytopenia and thrombosis), in which affected subjects produce platelet-activating antibodies that bind complexes of heparin/platelet membrane components and other molecules such as PF4, IL-8 and NAP-2, resulting in a prothrombotic and thrombocytopenic condition that can be life-threatening.

"Heparin-induced" as used herein refers to antibodies that result from exposure to heparin or those that recognize blood factors complexed with heparin as in spontaneous HIT, as indicative of HIT.

A "heparin-like compound" as used herein refers to a compound with a high negative charge such as a polyanion, a heparin derivative, a chemically modified heparin, a heparin-like glycosaminoglycan molecule, a proteoglycan containing multiple heparin or heparin-like glycosaminoglycans, lower-molecular-weight heparin, a synthetic glycosaminoglycan comprising at least 15 sugar units, or a synthetic heparin-like glycosaminoglycan any of which could be connected directly or through a spacer/linker molecule to a core molecule.

"Subject" as used herein refers to any animal. Typically, the animal is a mammal. A subject also refers to primates (e.g., humans, male or female; infant, adolescent, or adult), cows, sheep, goats, horses, dogs, cats, rabbits, rats, mice, fish, birds, and the like. In one embodiment, the subject is a primate. In one embodiment, the subject is a human. In one aspect, the subject is suspected of having pathogenic antibodies or platelet-activating antibodies. A "subject suspected of having platelet-activating antibodies" or "test subject" as used herein refers to a subject exhibiting clinical findings indicative of pathogenic antibodies, including, for example, a below-normal platelet count, a decrease in platelet count, enlargement or extension of a previously diagnosed blood clot, or the development of a new blood clot elsewhere in the body. Additional symptoms indicative of pathogenic antibodies include fever, rash, chills, high blood pressure, shortness of breath and chest pain. In one embodiment the platelet-activating antibody is an antibody capable of causing HIT. In another embodiment, the platelet-activating antibodies comprise platelet-activating heparin-induced thrombocytopenia antibodies. A "normal subject" refers to a subject not suffering from any aliment or not suspected of having platelet-activating antibodies.

A subject is "in need of" or "in need thereof" a diagnosis or treatment if such subject would benefit biologically, medically, or in quality of life from such diagnosis or treatment.

"Platelets," also known as "thrombocytes," as used herein refers to the anucleate fragments of megakaryocytes involved in blood coagulation, hemostasis, and blood thrombus formation. Human platelets are routinely isolated through a variety of methods including platelet apheresis, plateletpheresis, gel filtration, or differential centrifugation. Isolated platelets would be suitable, however, platelets from other sources, including washed platelets, unwashed platelets, platelet rich plasma or purified platelets, could also be used. In one embodiment, the platelets have been stabilized for storage by one or more of cooling, freezing, chemical storage, or lyophilization.

"Platelet activation" as used herein refers to the response of platelets when platelets encounter a "platelet activator" molecule that triggers activation, such as platelet activating antibodies, Thrombin Receptor Activating Peptide (TRAP), adenosine diphosphate (ADP), arachidonic acid, epinephrine, collagen, thrombin, thromboxane A2 (TxA2), thromboxane A2 (TXA2) mimetic U46619, calcium ionophore A23187, ristocetin, rhodocytin, among others. Platelet activation results in various changes to the platelets, including, for example, changes in markers associated with platelet activation, exocytosis of the dense granules and alpha granules, activation of the membrane enzyme phospholipase A2, changes in shape, aggregation, agglutination, changes in membrane potential, changes in integrin conformation, inter alia. Upon activation, platelets release granule contents including: adenosine triphosphate (ATP), adenosine diphosphate (ADP), 5-hydroxytryptamine (serotonin), thrombospondin, fibrinogen, CXCL12, thromboxanes, among other metabolites and proteins, which may be assessed by using different methodologies such as immunological assay, high-performance liquid chromatography (HPLC), fluorescence microscopy, or flow cytometry. Upon activation, platelets have a change in surface expression various markers including of P-Selectins, CD34, CD41, CD61, phosphatidyl serine, among others which may be assessed by using different methodologies such as immunological assay, high-performance liquid chromatography (HPLC), fluorescence microscopy, or flow cytometry. An "effective amount" as used herein refers to an amount of a compound that is sufficient to affect the desired outcome. In one embodiment, platelets are activated by administering an effective amount of one or more platelet activators as described herein.

Platelet activation levels may be measured using any method known in the art, such as, for instance, measuring levels of a marker found on or released from activated platelets in a test subject's blood sample as compared to levels of activated platelets in a normal subject's sample (e.g., a negative control sample) or a subject know to have platelet-activating antibodies or HIT (e.g., a positive control sample). Any marker known to be found on or released from activated platelets may be used to measure platelet activation, including, for example, one or more CD markers found on activated platelets (e.g., CD9, CD31, CD36, CD41, CD42, CD49b, CD61, CD62P, CD63, CD107, their isoforms, or any marker present on the outside of platelets), including the marker CD62P, also known as p-selectin. In addition, platelet activation can be measured by measuring any increased binding of immunoglobulin, phosphatidyl serine expression, platelet aggregation, intracellular levels of ionized calcium, changes in integrin conformation, release of platelet granule contents, changes in platelet membrane potential or platelet impedance, levels of Fc gamma receptor 2 cleavage fragments, or shape change of platelets.

"Increased in platelet activation" as used herein refers to an increase in platelet activation that is significantly different than that of the baseline platelet activation in a normal subject's blood sample or in comparison to known values or historical data obtained using the assays described herein. An increase in platelet activation is indicative of the patient having platelet-activating antibodies, such as antibodies that cause HIT. In one embodiment, the increase in platelet activation is at least two or three times the amount of baseline platelet activation in normal subject blood samples or historical data obtained for normal subjects using the methods described herein.

A "sample" as used herein refers to a specimen or culture obtained from a subject. Biological samples can be obtained from subjects and encompass fluids, solids, tissues, and gases. In one embodiment, the subject's sample is a blood sample. Blood samples include whole blood, plasma, serum, blood products such as platelet-rich plasma, or fractionated blood components, such as one of the Cohn fractions I-IV, or an antibody fraction. Typically, a sample of about 0.2 mL is needed for the method described herein.

"Labeled antibodies" as used herein refers to an antibody that is labeled with a radioisotope or fluorochrome such as phycoerythrin-conjugated mouse anti-human CD62p, allophycocyanin (APC)-conjugated AffiniPure F(ab')2 goat anti-human IgG, Fcγ specific, fluorescein (FITC)-conjugated F(ab')2 goat anti-human IgA, a chain specific, and the like. Additionally, one could use a variety of species to produce such antibodies including but not limited to mouse, rat, goat, sheep, rabbit, donkey, horse, bovine, porcine, and monkey. These antibodies can be either polyclonal or monoclonal antibodies.

"Fluorescently labeled" as used herein refers to a molecule (such as an antibody) that has been linked to a fluorochrome or other fluorescent molecules. In one embodiment, an antibody used in the method described is fluorescently labeled. Any method of fluorescent labeling known to the art may be used, including, for example, using fluorochromes. For instance, in one embodiment, antibodies having emission spectra at different wavelength maxima such as fluoresceine (519 nm), allophycocyanin (650 nm), or phycoerythrin (578), inter alia. Substitutions of fluorescently labeled secondary antibodies may be used distinguish the different fluorescent emission spectra. It is preferable to use fluorescently labeled antibodies having different emission wavelengths to ensure differentiation.

"Flow cytometry" as used herein is a laser-based, biophysical technology employed in cell counting, sorting, biomarker detection and protein engineering, by suspending cells in a stream of fluid and passing them by an electronic detection apparatus. It allows simultaneous analysis of the physical and/or chemical characteristics of up to thousands of particles per second. Flow cytometry is routinely used in the diagnosis of health disorders, especially blood cancers, but has many other applications in basic research, clinical practice, and clinical trials. In one embodiment described herein, "fluorescence-based flow cytometry", which is capable of detecting and quantifying fluorescently-labeled, cell bound probes, is used to detect pathogenic antibodies by measuring platelet activation (e.g., p-selectin expression) caused by such antibodies or measuring the binding of such antibodies to platelets, thus aiding in the diagnosis of pathogenic antibodies. However, other methods of detecting the fluorescently labeled antibodies known to the art may also be used. For instance, a Luminex type of platform would detect fluorochrome labeled beads or an ELISA plate reader capable of reading fluorescence could also be used.

"Instructions for use" as used herein refers to a publication, diagram, or any other medium of expression which is used to provide instructions or steps for performing the methods described herein. The instructions for use can be provided in printed form, affixed to a container which contains the kit materials, shipped together with the kit, or provided at an internet site.

"Room temperature," "RT," or "ambient temperature" as used herein refers to the typical temperature of a laboratory setting, 20±10° C.

"About" as used herein refers to any values, including both integers and fractional components that are within a variation of up to ±20% of the value modified by the term "about."

All ranges specified herein include the end points as discrete values as well as all integers within the specified range. For example, ranges specified such as "1 to 5" and "1-5" have equivalent meanings and include the discrete elements 1, 2, 3, 4, or 5, including fractional elements such as 2.5.

As used herein, the terms "a," "an," "the" and similar terms used in the context of the disclosure (especially in the context of the claims) are to be construed to cover both the singular and plural unless otherwise indicated herein or clearly contradicted by the context. In addition, "a," "an," or "the" means "one or more" unless otherwise specified.

Terms such as "include," "including," "contain," "containing," "having," and the like mean "comprising."

The term "or" can be conjunctive or disjunctive.

One embodiment described herein is a method for identifying platelet-activating antibodies in a subject's blood sample. In one embodiment, the method comprises: obtaining a blood sample from a subject suspected of having platelet-activating antibodies; combining a platelet releasate from one or more normal subjects with platelets from one or more normal subjects, and with the blood sample from the subject suspected of having platelet-activating antibodies and incubating the combination for a period of time; and measuring platelet activation; wherein platelet activation is indicative of the presence of platelet-activating antibodies in the blood sample from the subject suspected of having platelet-activating antibodies. In one aspect, the platelet-activating antibodies comprise platelet-activating heparin-induced thrombocytopenia (HIT) antibodies.

In one aspect, the sample from the subject suspected of having platelet-activating antibodies (e.g., test subject) is combined with a platelet releasate from one or more normal subjects and platelets from one or more normal subjects. The platelet release can be prepared as described herein. The platelets from one or more normal subjects comprises one or more of isolated platelets, platelet-rich plasma, or washed platelets. The platelets may have been stabilized for storage by one or more of cooling, freezing, chemical storage, or lyophilization. The test subject's sample can comprise whole blood, plasma, serum, or fractionated blood. The mixture is incubated for a period of time at a specific temperature. The incubation period of time can be for about 5 min. to about 5 hours at a temperature from about 15° C. to about 37° C. In another aspect, the period of time is about 20 minutes to about 1 hour. In one aspect, the incubation temperature is ambient temperature or about 20±10° C. The platelet activation is measured following the incubation by various methods known in the art and described herein. An increase in platelet activation is indicative of the patient having platelet-activating antibodies, such as antibodies that cause HIT.

Another embodiment described herein is a method for identifying platelet-activating antibodies in a subject's blood sample, the method comprising: obtaining a blood sample from a subject suspected of having platelet-activating antibodies; combining a platelet releasate from one or more normal subjects with platelets from one or more normal subjects and incubating the combination for a first period of time; combining the blood sample from a subject suspected of having platelet-activating antibodies with the combination of platelet releasate and platelets from one or more normal subjects and incubating the second combination for a second period of time; measuring platelet activation; wherein platelet activation is indicative of the presence of platelet-activating antibodies in the blood sample from the subject suspected of having platelet-activating antibodies. In one aspect, the platelet-activating antibodies comprise platelet-activating heparin-induced thrombocytopenia (HIT) antibodies.

In one aspect, a platelet releasate from one or more normal subjects is combined with platelets from one or more normal subjects and the combination is incubated for a first period of time at a specific temperature. The platelet release can be prepared as described herein. The platelets from one or more normal subjects comprises one or more of isolated platelets, platelet-rich plasma, or washed platelets. The first period of time is about 5 min. to about 1 hour and the temperature is at a temperature from about 15° C. to about 37° C. In another aspect, the period of time is about 20 minutes to about 1 hour. In one aspect, the incubation temperature is ambient temperature or about 20±10° C. Following the incubation of the platelet releasate from one or more normal subject with platelets from one or more normal subjects, the test subject's sample is combined with the normal releasate/normal platelet combination. This mixture is incubated for a second period of time at a specific temperature. In one aspect, the test subject sample/releasate/platelet combination is incubated for about 15 min. to about 5 hours at a temperature from about 15° C. to about 37° C. In another aspect, the period of time is about 30 min. to about 2 hours. In one aspect, the incubation temperature is ambient temperature or about 20±10° C. The platelet activation is measured following the incubation by various methods known in the art and described herein. An increase in platelet activation relative to baseline, a normal subject, or historical data is indicative of the patient having platelet-activating antibodies, such as antibodies that cause HIT.

In another embodiment, the amount of platelet-activating antibodies in the patient sample is determined by measuring one or more markers of platelet activation including analyzing the release of platelet granule components; detecting the expression of cell surface markers; detecting increase in expression of p-selectin on the platelet; detecting an increase in binding of annexin V to the platelet, detecting an increased proteolytic cleavage of the platelet membrane protein Fc gamma RII (CD32); detecting a change in platelet shape; detecting an increased level of ionized calcium in the platelet cytoplasm; detecting changes in expression levels of one or more CD markers found on activated platelets; detecting a change in platelet integrin conformation; detecting a change in platelet membrane potential; detecting a change in platelet impedance; detecting platelet agglutination; detecting platelet aggregation; detecting activated-platelet metabolic state; or detecting activated-platelet metabolites or byproducts.

In one embodiment, measuring platelet activation is performed by measuring platelet activation comprises analyzing the expression of cell surface markers that are expressed upon platelet activation using fluorescence-based flow cytometry, radioimmunoassays (RIA), or enzyme-linked immunosorbent assays (ELISAs).

In one embodiment, the method described herein may further comprise a fluorescence-based flow cytometry) assay adding one or more fluorescently labeled antibodies. In one embodiment, one antibody is specific for a platelet-specific marker such as CD41 and another antibody is specific for a surface marker of platelet activation such as anti-p-selectin antibody. In one aspect, the antigen used to identify platelets for flow cytometric analysis is CD9, CD31, CD36, CD41, CD42, CD49b, CD61, CD62P, CD63, CD107, their isoforms, or additional markers present on the cell surface of platelets. Platelets can also be identified in flow cytometry by their forward and side-scatter properties.

In one embodiment, the method may further comprise a fluorescence-based flow cytometry assay adding a fluorescently labeled probe specific for a surface marker of platelet activation such as an anti-p-selectin antibody.

Figure 1:
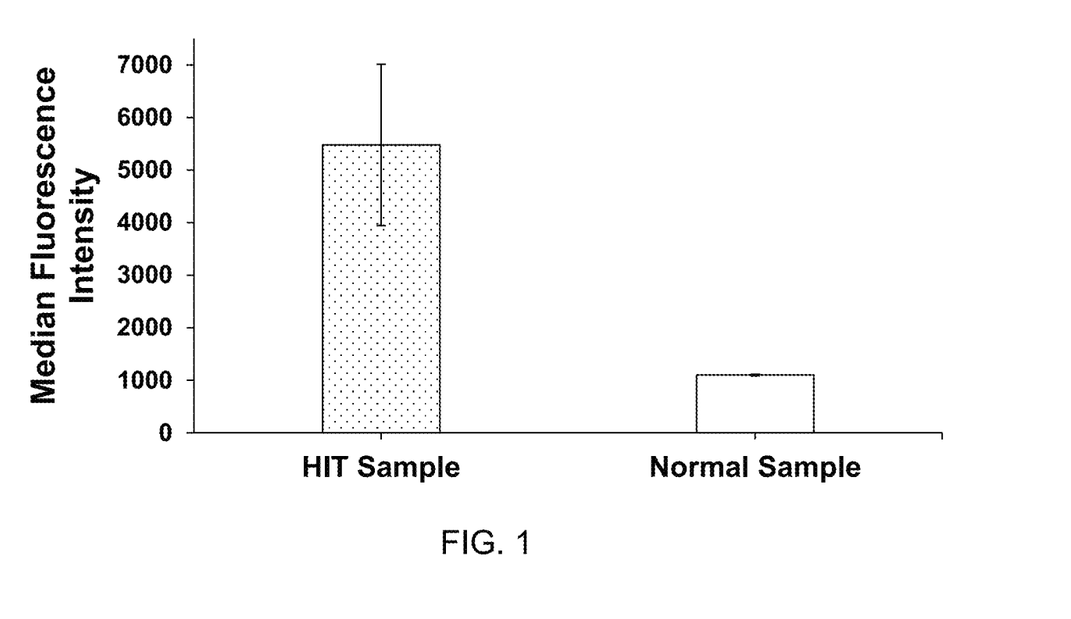
FIG. 1. Platelet-releasate dependent platelet activation. Heparin-induced thrombocytopenia (HIT) sample (hashed bar) or normal sample (open bar) were added to platelets incubated with platelet releasate. Platelet activation was assessed by measuring CD62p (p-selectin) expression on the platelet surface using a fluorescently labeled anti-CD62p antibody by fluorescence-based flow cytometry. Values shown are the mean of duplicate determinations. Error bars depict standard error of the mean. Data are shown in Table 1.
Figure 2:
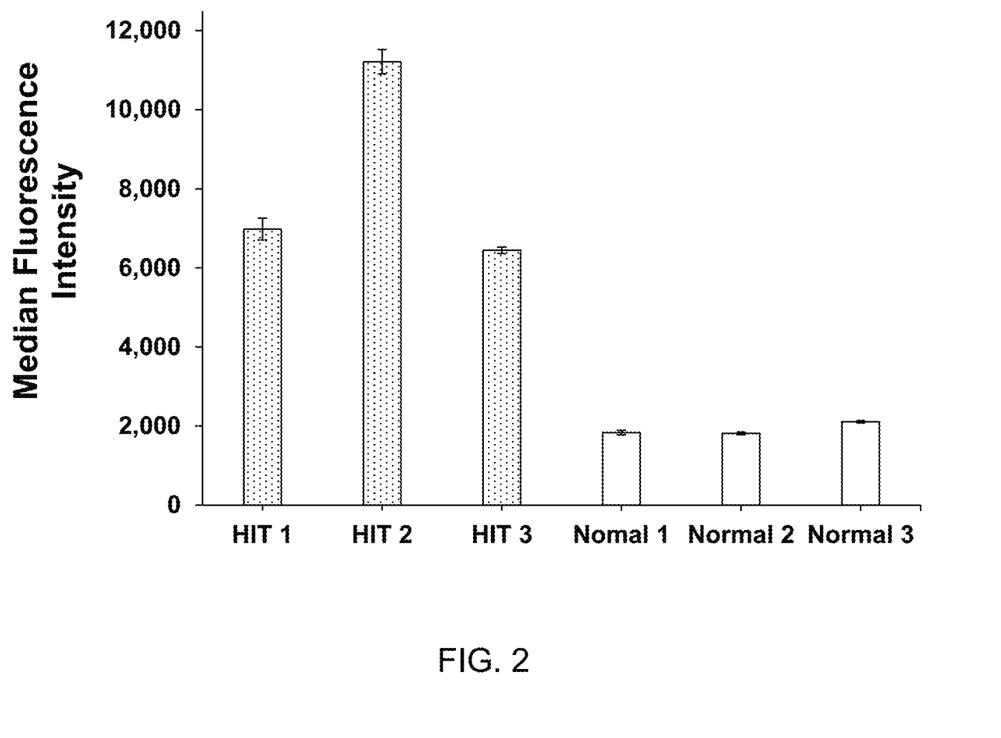
FIG. 2. A platelet-releasate dependent platelet activation assay differentiates HIT from normal samples. Three HIT (hashed bar) or three normal (open bar) blood samples were added to platelets incubated with DEAE-adsorbed platelet releasate. Platelet activation was assessed by measuring CD62p (p-selectin) expression on the platelet surface using a fluorescently labeled anti-CD62p antibody by fluorescence-based flow cytometry. Values shown are the mean of duplicate determinations. Error bars depict standard error of the mean. Data are shown in Table 2.

In another embodiment, measuring platelet activation is performed by identifying cell surface receptors that are expressed upon platelet activation. The cell surface markers can comprise one or more of selectins, integrins, or immunoglobulins. In one aspect, the cell surface marker is a selectin such as p-selectin (CD62P). This occurs because alpha granules expressing high levels of CD62P inside the platelets migrate to the surface and fuse in order to release their contents into the bloodstream. This causes the rise of CD62P on the surface of the activated platelets. FIGS. 1 and 2 provide examples of the detection of platelet-activating antibodies (e.g., HIT antibodies) in a test subject's blood sample using fluorescently-labeled antibodies that recognize p-selectin (CD62P) expression on activated platelet cells' surface. An increase in p-selectin median fluorescence intensity (MFI) of >5000 relative to a normal subject's sample (MFI of ~1100) is considered positive in the assay depicted in FIGS. 1-2. In general, determination can be considered positive when the ratio of signal (such as p-selectin expression) obtained with the test subject's sample exceeds the signal obtained using a normal subject's sample or historical data by at least 2-fold, and preferably at least 3-fold or greater.

In another embodiment, measuring platelet activation comprises analyzing the release of platelet granule components such as metabolites or byproducts that are produced during platelet activation.

In another embodiment, measuring platelet activation comprises analyzing the release of platelet granule components where the platelets were incubated with a labeled molecule or probe that is uptaken and subsequently released upon platelet activation. For example, radiolabeled or biotinylated 5-hydroxytryptaime (serotonin) can be incubated with the normal subject's platelets prior to or in conjunction with the incubation with the normal platelet releasate. Upon addition of a sample from a subject having platelet activating antibodies, the platelets become activated and release the radiolabeled or biotinylated serotonin. This can be measured using various methods for identifying labeled serotonin known in the art such as ELISA, radioimmunoassays, scintillation counting, HPLC, inter alia.

In another embodiment, measuring platelet-activation caused by platelet activating antibodies may be measured by observing increased platelet aggregation or agglutination by one of many methods known to one of skill in the art.

In one embodiment, the methods described herein are performed using a high-dose heparin control, where heparin, heparin-like molecules, or a polyanionic compound is added to the test subject's sample/releasate/platelet combination at a concentration of about 5 U/mL to about 200 U/mL. In one aspect, the heparin concentration is about 100 U/mL. In another aspect, a heparin control can be used to confirm that antibodies in the sample from a subject that is suspected of having platelet-activating antibodies caused platelet activation in the assays described herein. For example, when an assay comprising a heparin control demonstrates that a sample which has platelet-activating antibodies decreases to baseline levels, this indicates that the platelet activation was specifically mediated by the antibodies of the subject that is suspected of having platelet-activating antibodies.

In another embodiment, the methods described herein may be performed in the presence of a low-dose heparin, heparin-like molecules, or polyanionic compounds. In one aspect, the heparin, heparin-like molecules, or polyanionic compounds are present at a concentration of about 0.05 U/mL to about 2.5 U/mL. In the assays described herein, these heparin or heparin-like compounds are not required to measure the quantity of platelet-activating antibodies.

In another embodiment, the platelet activation is compared to one or more controls comprising blood from one or more normal subjects (e.g., negative control) or blood from one or more subjects diagnosed as having platelet-activating antibodies, such as HIT (e.g., positive control), or historical data obtained from normal subjects or HIT subjects using the methods described herein. In one aspect, platelet activation is indicated by at least a 2-fold increase in the measured signal as compared to that of baseline, e.g., the normal negative control sample or historical data thereof. In another embodiment, the platelet activation is compared to historical data obtained using the assay(s) described herein without comparing each result to a normal subject or a subject diagnosed as having platelet-activating antibodies, such as HIT.

Another embodiment described herein is a method of preparing a platelet releasate, the method comprising: obtaining platelets form one or more normal subjects; activating platelets from one or more normal subjects by the addition of an effective amount of a platelet activator and incubating for a period of time; collecting material released from the platelets upon activation to obtain a platelet releasate. In one aspect, the period of time is from about 15 min. to about 4 hours at a temperature of about 15° C. to about 37° C. In another aspect, the period of time is about 30 min. to about 2 hours. In one aspect, the incubation temperature is ambient temperature or about 20±10° C. In another aspect, the method further comprises incubating the isolated platelet releasate at about 40° C. to about 75° C. for about 5 min. to about 10 hours. In another aspect, the incubation is at about 60° C. for about 1 hour. In another aspect, the method further comprises removing negatively charged ions from the platelet releasate with an anion-exchanger to obtain an anion-exchanger adsorbed platelet releasate. The anion exchange can comprise a resin or cartridge and can be performed on a column or in batch. The anion exchanger can comprise diethylaminoethyl (DEAE), quaternary amine (Q), Dowex™, Dionex™, or other anion exchange resins or cartridges known in the art. In one aspect, the platelet releasate is incubated with the anion-exchanger for about 5 min. to about 4 hours.

In another embodiment, the normal platelets are activated using a platelet activator. The platelet activator can comprise one or more of Thrombin Receptor Activating Peptide (TRAP), adenosine diphosphate (ADP), arachidonic acid, epinephrine, collagen, thrombin, thromboxane A2 (TxA2), thromboxane A2 (TXA2) mimetic U46619, calcium ionophore A23187, ristocetin, or rhodocytin.

Another embodiment is a platelet releasate produced using the methods described herein.

Another embodiment is the use of the platelet releasate described herein for identifying platelet-activating antibodies in a blood sample from a subject suspected of having platelet-activating antibodies or the analysis of normal subjects to obtain reference data.

Another embodiment is a lateral flow immunochromatographic assay for detecting heparin-induced thrombocytopenia antibodies using the methods described herein.

Another embodiment described herein is a kit for identifying platelet-activating antibodies in a subject's blood sample, the kit comprising one or more of: (a) a container and means for collecting blood from a subject suspected of having platelet-activating antibodies; (b) a container comprising a platelet releasate from one or more normal subjects; (c) a container comprising platelets from one or more normal subjects; (d) a container for combing (a)-(c); (e) reagents for analyzing the presence of platelet-activating antibodies in the blood from a subject suspected of having platelet-activating antibodies; (f) one or more control samples comprising blood from a normal subject or blood from a subject diagnosed as having platelet-activating antibodies; or (g) instructions or directions for use.

Another embodiment described herein is a kit for preparing a platelet releasate, the kit comprising one or more of: (a) a container and means for obtaining blood from one or more normal subjects; (b) a means for isolating platelets from the one or more normal subject's blood; (c) a container for activating platelets; (d) a platelet activator; (e) an anion-exchange resin or cartridge; (f) a means for collecting the platelet releasate; or (f) instructions or directions for use.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All the various embodiments, aspects, and options disclosed herein can be combined in any variations or iterations. The scope of the compositions, formulations, methods, and processes described herein include all actual or potential combinations of embodiments, aspects, options, examples, and preferences herein described. The compositions, formulations, or methods described herein may omit any component or step, substitute any component or step disclosed herein, or include any component or step disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the specification discloses and describes merely exemplary embodiments. All patents and publications cited herein are incorporated by reference herein for the specific teachings thereof.

EXAMPLES

Example 1

Method Overview

Step 1: Platelet Releasate Preparation

"Platelet releasate" as described herein is prepared by activating normal human platelets with a platelet activator. The source of platelets may be from a blood sample freshly drawn from a normal subject or platelets obtained from a blood donation from a normal subject. The platelet activator may be one or more chemicals or molecules described herein. Experiments described herein typically utilized the platelet activator Thrombin Receptor Activating Peptide (TRAP). Optimally, the platelet releasate was also incubated with positively charged beads (e.g., DEAE Sepharose™) so that substances in platelet releasate (e.g., glycosaminoglycans) that may interfere with the reaction are removed. The platelet releasate was typically heated to 56° C. for 1 hour.

Step 2: Incubate the platelet releasate with platelets obtained from a normal subject at about 20° C. for about 20 min.

Step 3: Incubate platelet releasate treated platelets from Step 2 with a subject's blood sample at about 20° C. for about 60 min.

Step 4: Assess platelet activation.

Platelet activation was measured by fluorescence-based flow cytometry.

FIG. 1 shows the analysis results of a test subject with results indicative of HIT as compared to a normal subject's sample using platelet releasate. Data are shown in Table 1.

TABLE 1

Results Using Platelet Releasate

| Test Subject's Mean Florescent Intensity | Normal Subject Mean Fluorescent Intensity |
|---|---|
| 5480 ± 1536* | 1100 ± 16* |

*Standard errors of the mean.

FIG. 2 shows the analysis results of 3 test subjects with results diagnostic of HIT as compared to 3 normal subjects using DEAE-Sepharose™ adsorbed platelet releasate. Data are shown in Table 2.

TABLE 2

Results Using DEAE-Adsorbed Platelet Releasate

| Test Subject's Mean Florescent Intensity | | Normal Subject Mean Fluorescent Intensity | |
|---|---|---|---|
| Test 1 | 6981 ± 277* | Normal 1 | 1835 ± 57* |
| Test 2 | 11214 ± 311* | Normal 2 | 1815 ± 34* |
| Test 3 | 6446 ± 80* | Normal 3 | 2111 ± 31* |

*Standard errors of the mean.

Platelet activation can be measured by other methods. For example, prior to testing, platelets can be incubated with a labeled molecule that is uptaken prior to the platelet treatment with releasate. Then during the activation reaction, this material is released by the platelets which can then be measured easily. For example, biotinylated serotonin can be incubated with platelets and is uptaken. Then these serotonin-loaded platelets are treated with platelet releasate, followed by incubation with the test subject's sample. If the test subject's sample contains platelet-activating HIT antibodies, the biotinylated serotonin will be released and detected.

Example 2

Platelet Releasate Preparation

Platelets can be drawn fresh from a blood donor or may be obtained from a unit of platelets obtained from a whole blood or apheresis platelet collection. Platelet rich plasma from a blood donation unit (180 mL) obtained from a normal subject was combined with 20 mL Anticoagulant Citrate Dextrose-Solution A (ACD-A) and 200 µL prostaglandin E-1(PGE1) (50 µg/mL, 50 ng/mL final). The mixture was centrifuged at 100×g for 15 min. The supernatant solution (160 mL) was collected and centrifuged at 1000×g for 15 min. The supernatant solution was removed and discarded; the pellet was resuspended in 3 mL Phosphate Buffered Saline, pH 7.4 (PBS) containing 1% Bovine Serum Albumin (BSA). The platelets were counted and diluted to a concentration of $2\times10^6$ platelets/µL in a volume of 15 mL with PBS containing 1% BSA. Thrombin Receptor Activating Peptide (TRAP), 240 µL at 125 µg/mL, was added to a final TRAP concentration of 2 µg/mL. The combination was incubated for 1 hour at room temperature on a shaker. After incubation, the solution was centrifuged at 1000×g for 15 min. The supernatant solution was collected (platelet releasate).

Anion Exchanger Adsorption and Heat Treatment

DEAE Sepharose™ was prepared by dispensing 1 mL of diethylaminoethanol (DEAE) Sepharose™ in a 15 mL conical tube and adding deionized $H_2O$ to a total volume of 15 mL. The resin was centrifuged at 1000×g for 15 min. The supernatant was discarded, and the resin was resuspended in 15 mL PBS. The resin was centrifuged at 1000×g for 15 min. The PBS wash was performed at least one additional time. The PBS-washed DEAE resin was combined with 5 mL platelet releasate and incubated at room temperature for 3 hours with shaking. The resin-releasate mixture was centrifuged at 1500×g for 15 minutes. The DEAE-adsorbed releasate supernatant solution was collected. The DEAE-adsorbed releasate was incubated at about 56° C. water bath for about 1 hour. The DEAE-adsorbed releasate (with or without heat-treatment) was stored at 4° C. or −20° C. until use.

Platelet Activation and Flow Cytometry

Platelet rich plasma (9 mL) was collected from a blood donation unit obtained from a normal subject and 1 mL ACD-A and 10 µL PGE1 (50 µg/mL stock, 50 ng/mL final), are added. The mixture was centrifuged at 100×g 15 for min. The supernatant (3 mL) was collected and centrifuged at 1000×g for 15 minutes. The supernatant was removed from the 3 mL aliquot and resuspended in 600 µL PBS containing 1% BSA and counted with a hemocytometer. The platelets were diluted to $2.5\times10^4$ platelets/µL with 35 µL of platelet releasate in a final volume of 40 µL and incubated at 20 minutes room temperature. Test subject serum (10 µL) was added to a 1:5 dilution of the releasate in a total reaction volume of 50 µL and incubated for 60 minutes at room temperature. Phycoerythrin labeled anti-CD62p (e.g., anti-p-selectin) antibody (5 µL of 25 µg/mL; 2.5 µg/mL final concentration) was added and the reaction incubated for 20 minutes at room temperature. PBS containing 1% BSA (150 µL) was added and the resulting solution was analyzed using flow cytometry gating platelets based on forward scatter (FSC-A) and side scatter (SSC-A) and the median fluorescence intensity was recorded.

What is claimed:

1. A method for identifying platelet-activating heparin-induced thrombocytopenia (HIT) antibodies in a blood sample from a subject suspected of having platelet-activating HIT antibodies, the method comprising:
    obtaining a blood sample comprising serum, plasma, or fractionated blood from a subject suspected of having platelet-activating HIT antibodies;
    obtaining platelets from one or more normal subjects;
    obtaining a platelet releasate from the platelets from one or more normal subjects by activating the platelets from the one or more normal subjects with a platelet activator and collecting material released from the activated platelets, forming a platelet releasate;
    combining the platelet releasate from the one or more normal subjects, the platelets from the one or more normal subjects, and the sample from the subject suspected of having platelet-activating antibodies, forming a combined sample, and incubating the combined sample for about 5 min. to about 4 hours; and
    measuring platelet activation in the combined sample;
    wherein platelet activation in the combined sample is indicative of the presence of platelet-activating HIT antibodies in the blood sample from the subject suspected of having platelet-activating antibodies.

2. The method of claim 1, wherein the platelet releasate is prepared by:
    activating platelets from the one or more normal subjects by the addition of a platelet activator;
    collecting material released from the activated platelets and incubating at about 40° C. to about 75° C. for about 15 min. to about 10 hours; and
    contacting the material released from the activated platelets with an anion-exchanger for about 15 min. to about 4 hours and obtaining a platelet releasate.

3. The method of claim 1, wherein measuring platelet activation comprises one or more of: analyzing the release of platelet granule components; detecting the expression of platelet cell surface markers that are expressed upon platelet activation; detecting increase in expression of p-selectin on the platelet; detecting an increase in binding of annexin V to the platelet, detecting an increased proteolytic cleavage of the platelet membrane protein Fc gamma RII (CD32); detecting a change in platelet shape; detecting an increased level of ionized calcium in the platelet cytoplasm; detecting changes in expression levels of one or more cell surface markers indicative of activated platelets; detecting a change in platelet integrin conformation; detecting a change in platelet membrane potential; detecting a change in platelet impedance; detecting platelet agglutination; detecting platelet aggregation; detecting activated-platelet metabolic state; or detecting activated-platelet metabolites or byproducts.

4. The method of claim 3, wherein the platelet cell surface markers comprise one or more of selectins, integrins, or immunoglobulins.

5. The method of claim 3, wherein the platelet cell surface markers comprise p-selectin.

6. The method of claim 1, wherein measuring platelet activation comprises analyzing the expression of platelet cell surface markers that are expressed upon platelet activation using flow cytometry, radioimmunoassays (RIA), or enzyme-linked immunosorbent assays (ELISAs).

7. The method of claim 1, wherein measuring platelet activation comprises analyzing the release of platelet granule components.

8. The method of claim 1, further comprising combining heparin or a heparin-like compound with the platelet releasate from one or more normal subjects, platelets from one or more normal subjects, and the blood sample from the subject suspected of having platelet-activating HIT antibodies.

9. The method of claim 8, wherein the heparin or heparin-like compound has a final concentration of about 0.05 U/mL to about 200 U/mL.

10. The method of claim 1, wherein the platelets from one or more normal subjects comprises one or more of isolated platelets, platelet-rich plasma, or washed platelets.

11. The method of claim 1, wherein the platelets have been stabilized for storage by one or more of cooling, freezing, chemical storage, or lyophilization.

12. The method of claim 1, wherein the platelet activation is compared to one or more controls comprising blood from a normal subject, historical data, or blood from a subject diagnosed as having platelet-activating HIT antibodies.

13. A method for identifying platelet-activating heparin-induced thrombocytopenia (HIT) antibodies in a blood sample from a subject suspected of having platelet-activating HIT antibodies, the method comprising:
obtaining a blood sample comprising serum, plasma, or fractionated blood from a subject suspected of having platelet-activating HIT antibodies;
obtaining platelets from one or more normal subjects;
obtaining a platelet releasate from the platelets from one or more normal subjects by activating the platelets from one or more normal subjects with a platelet activator, collecting material released from the activated platelets, and contacting the material released from the activated platelets with an anion-exchanger forming a platelet releasate;
combining the platelet releasate with platelets from one or more normal subjects, forming a first combined sample and incubating the first combined sample for about 5 min. to about 1 hour;
combining the subject sample with the first combined sample, forming a second combined sample, and incubating the second combined sample for 5 min. to about 5 hours;
measuring platelet activation in the second combined sample;
wherein platelet activation in the second combined sample is indicative of the presence of platelet-activating HIT antibodies in the blood sample from the subject suspected of having platelet-activating antibodies.

14. The method of claim 13, wherein the platelet releasate is prepared by:
activating platelets from one or more normal subjects by the addition of a platelet activator;
collecting material released from the activated platelets and incubating at about 40° C. to about 75° C. for about 15 min. to about 10 hours; and
contacting the material released from the activated platelets with an anion-exchanger for about 15 min. to about 4 hours and obtaining the platelet releasate.

15. The method of claim 13, wherein measuring platelet activation comprises one or more of: analyzing the release of platelet granule components; detecting the expression of platelet cell surface markers that are expressed upon platelet activation; detecting increase in expression of p-selectin on the platelet; detecting an increase in binding of annexin V to the platelet, detecting an increased proteolytic cleavage of the platelet membrane protein Fc gamma RII (CD32); detecting a change in platelet shape; detecting an increased level of ionized calcium in the platelet cytoplasm; detecting changes in expression levels of one or more cell surface markers indicative of activated platelets; detecting a change in platelet integrin conformation; detecting a change in platelet membrane potential; detecting a change in platelet impedance; detecting platelet agglutination; detecting platelet aggregation; detecting activated-platelet metabolic state; or detecting activated-platelet metabolites or byproducts.

16. The method of claim 15, wherein the platelet cell surface markers comprise one or more of selectins, integrins, or immunoglobulins.

17. The method of claim 15, wherein the platelet cell surface markers comprise p-selectin.

18. The method of claim 13, wherein measuring platelet activation comprises analyzing the expression of platelet cell surface markers that are expressed upon platelet activation using flow cytometry, radioimmunoassays (RIA), or enzyme-linked immunosorbent assays (ELISAs).

19. The method of claim 13, wherein measuring platelet activation comprises analyzing the release of platelet granule components.

20. The method of claim 13, further comprising combining heparin or a heparin-like compound with the platelet releasate from one or more normal subjects, platelets from one or more normal subjects, and the blood sample from the subject suspected of having platelet-activating HIT antibodies.

21. The method of claim 20, wherein the heparin or heparin-like compound has a final concentration of about 0.05 U/mL to about 200 U/mL.

22. The method of claim 13, wherein the platelets from one or more normal subjects comprises one or more of isolated platelets, platelet-rich plasma, or washed platelets.

23. The method of claim 13, wherein the platelets have been stabilized for storage by one or more of cooling, freezing, chemical storage, or lyophilization.

24. The method of claim 13, wherein the platelet activation is compared to one or more controls comprising blood from a normal subject, historical data, or blood from a subject diagnosed as having platelet-activating HIT antibodies.

25. A kit for identifying platelet-activating heparin-induced thrombocytopenia (HIT) antibodies in a blood sample from a subject configured for use with the method of claim 1 or claim 13, wherein the subject is suspected of having platelet-activating heparin-induced thrombocytopenia, the kit comprising one or more of:
(a) a container and means for collecting blood from a subject suspected of having platelet-activating HIT antibodies;
(b) a container comprising a platelet releasate from one or more normal subjects;
(c) a container comprising platelets from one or more normal subjects;
(d) a container comprising heparin or other polyanion;
(e) a container for combining (a)-(d);
(f) reagents for analyzing platelet activation;
(g) one or more control samples comprising blood from a normal subject or blood from a subject diagnosed as having platelet-activating HIT antibodies; or
(h) instructions or directions for use.

26. A kit for preparing a platelet releasate configured for use with the method of claim 1 or claim 13, the kit comprising one or more of:
(a) a container and means for obtaining blood from one or more normal subjects;
(b) a means for isolating platelets from the one or more normal subject's blood;
(c) a container for activating platelets;
(d) a platelet activator;
(e) an anion-exchange resin or cartridge;

(f) a means for collecting the platelet releasate; or
(f) instructions or directions for use.

* * * * *